United States Patent [19]

Song

[11] Patent Number: 5,997,908
[45] Date of Patent: *Dec. 7, 1999

[54] PROSTATE EXTRACT SUPPLEMENTED WITH ZINC

[76] Inventor: Moon K. Song, 10922 Yolanda Ave., Northridge, Calif. 91326

[*] Notice: This patent is subject to a terminal disclaimer.

[21] Appl. No.: 08/718,299

[22] PCT Filed: Mar. 17, 1994

[86] PCT No.: PCT/US94/02909

§ 371 Date: Mar. 24, 1997

§ 102(e) Date: Mar. 24, 1997

[87] PCT Pub. No.: WO95/24911

PCT Pub. Date: Sep. 21, 1995

Related U.S. Application Data

[63] Continuation-in-part of application No. 08/179,761, Jan. 7, 1994, Pat. No. 5,411,748, which is a continuation of application No. 07/964,879, Oct. 22, 1992, abandoned.

[51] Int. Cl.$^6$ .......................... A61K 33/30; A61K 35/48
[52] U.S. Cl. .......................... 424/559; 424/643; 514/560; 514/494
[58] Field of Search .................................... 424/559, 643; 514/560, 494

[56] References Cited

U.S. PATENT DOCUMENTS 4,302,447 11/1981 Horrobin ................................ 424/643

FOREIGN PATENT DOCUMENTS 1740004 6/1992 U.S.S.R. .

OTHER PUBLICATIONS

Langley et al., Genitourinary Medicine 63(4): 264–267 (Aug. 1987). Abstract.

M.K. Song, et al.; Journal of Nutrition; vol. 109, No. 12, Dec. 1979; pp. 2152–2158; "Evidence for an Important Role of Prostaglandins E$_2$ and F$_2$ in the Regulation of Zinc Transport in the Rat".

Moon K. Song, et al.; Comp.Biochem.Physiol., vol. 101A, No. 3, pp. 477–481, 1992; "Prostaglandin Interacts with Steriod Sex Hormones in the Regulation of Intestinal Zinc Transport".

M.K. Song, et al.; pp. E99–E–105; "Role of prostaglandin E$_2$ in zinc absorption in the rat".

M.K.Song, et al.; Life Sciences, vol. 33, pp. 2399–2408; "A New Low–Molecular–Weight Calcium–Binding Ligand in Rat Small Intestine".

N.F. Adham, et al.; Nutrition and Metabolism; vol. 24: 281–290 (1980); "Effect of Calcium and Copper on Zinc Absorption in the Rat".

Moon K. Song, et al.; Comp.Biochem.Physiol.; vol. 85C, No. 2, pp. 283–289; 1986; "Relative Zinc–Binding Activities of Ligand in the Cytosol of Rat Small Intestine".

Moon K. Song; Comp.Biochem.Physiol.; vol. 87A, No. 2, pp. 223–230, 1987; "Low–Molecular–Weight Zinc–Binding Ligand: A Regulatory Modulator for Intestinal Zinc Transport".

Moon K. Song, et al.; Biological Trace Element Research; vol. 11, 1986; pp. 75–88; "Levels and Distribution of Zinc, Copper, Magnesium, and Calcium in Rats Fed Different Levels of Dietary Zinc".

M.K. Song., et al.; Biochemical Archives, vol. 1, pp. 75–83; "Metabolic Influences on Intestinal Zinc Uptake in Rats".

Moon K. Song, et al.; Biological Trace Element Research; vol. 6, 1984; "Metabolism of Zinc–Binding Ligands in Rat Small Intestine".

George Y. Luh, et al.; Comp.Biochem.Physiol.; vol. 91B, No. 3, pp. 569–576, 1988; "Characterization of the Low Mol. Wt Zinc–Binding Ligand From Rat Small Intestine by Comparison to the Organic Zinc–Binding Ligands".

S. Arver; Acta Physiol Scand 1982, 116:67–73; "Zinc and zinc ligands in human seminal plasma".

M. Schneir, et al.; Diabetes, vol. 31, May 1982; "Streptozotocin–induced Diabetic Rat Enhanced Catabolism of collagen Formed Both Before and During the Diabetic State".

M. Johnson, et al.; The Lancet I: 325–326, 1979; "Vascular Prostacyclin May be Reduced in Diabetes in Man".

K. Engelbart, et al.; Virchows Arch.Abt.B.Zellpath. 4, 294–302 (1970); "Uber das funktionelle Verhalten von Zink und Insulin in den B–Zellen des Rattenpankreas".

J.L. Marx; Science, vol. 225, pp. 1381–1383; Sep. 1984; "Diabetes—A Possible Autoimmune Disease".

L. Hurley, et al.; The Lance I: 1979; pp. 677–678; "Zinc Citrate, Human Milk and Acrodermatitis Enteropathica".

S. Katayama, et al.; Hypertension Program Unit, vol. 7, No. 4, Jul.–Aug. 1985; pp. 554–561; "Hypertension in Experimental Diabetes Mellitus Renin–Prostaglandin Interaction".

W.T. Johnson, et al.; J. Nutr. 115: 1217–1227, 1985; "Intestinal Absorption and Excretion of Zinc in Streptozotocin––Diabetic Rats as Affected by Dietary Zinc and Protein".

R.P. Robertson, et al.; Journal of Clinical Investigation, vol. 60, Sep. 1977; pp. 747–753; "A role for Prostaglandin E in Defective Insulin Secretion and Carbohydrate Intolerance in Diabetes Mellitus".

G.W. Evans, et al.; J.Nutr. 110:1076–1080, 1980; "Zinc Absorption in Rats Fed a Low–Protein Diet and a Low–Protein Diet Supplemented with Tryptophan or Picolinic Acid".

H.E. Harrison, et al.; Life Sciences, vol. 23, pp. 351–356; "Decreased Vascular Prostacyclin in Experimental Diabetes".

(List continued on next page.)

Primary Examiner—Jean C. Witz
Attorney, Agent, or Firm—Knobbe Martens Olson & Bear, LLP

[57] ABSTRACT

A composition of matter comprising crystalline zinc chelated with animal prostate extract provides a convenient source of both fatty acids and zinc for dietary and therapeutic purposes. The pharmaceutical composition is useful for the treatment of diabetes.

8 Claims, 3 Drawing Sheets

OTHER PUBLICATIONS

M.K. Chooi, et al.; Nutr.Metabol.20: 135–142 (1976); "Influence of Age and Sex on Plasma Zinc Levels in Normal and Diabetic Individuals".

Biochemical Medicine 23, pp. 231–235; 1980; *Short Communications;* "Altered Synthesis of Prostaglandins in Platelet and Aorta from Spontaneously Diabetic Wistar Rats".

R.J. Illman, et al.; Atherosclerosis, 59, 1986, pp. 313–321; "Time–Course of Changes in Plasma Lipids in Diabetic Rats Fed Diets High in Fish or Safflower Oils".

A. Reznikov, et al.; Endocrinologia Experimentalis, vol. 24, 1990; pp. 437–447; "Nonsteroid Antiandrogen Inhibiting Effect on Testosterone Metabolism in Rat Prostate and Liver".

H.E. Harrison, et al.; Diabetologia, 18, pp. 65–68, 1980; "Effect of Insulin Treatment on Prostacyclin in Experimental Diabetes".

G.F. Bottazzo, et al.; Immunology Today, vol. 5, No. 8, 1984, pp. 230–231; "Hypotheses on Genetic Contributions to the Aetiology of Diabetes Mellitus".

D.A. Scott, et al.; Connaught Laboratories, University of Toronto, Toronto, Canada; pp. 725–728; "The Insulin and The Zinc Content of Normal and Diabetic Pancreas".

B. Koletzko, et al.; Eur.J.Pediatr (1985) 143: 310–314; "Fatty acid composition of plasma lipids in acrodermatitis enteropathica before and after zinc supplementation".

F.K.Ghishan, et al.; Life Sciences, vol. 32, pp. 1735–1741; "Intestinal Transport of Zinc in the Diabetic Rat".

W.B. Kinlaw, M.D., et al.; The American Journal of Medicine, vol. 75, Aug. 1983, pp. 273–277; "Abnormal Zinc Metabolism in Type II Diabetes Mellitus".

Moon K. Song, Ph.D., et al.; The American Journal of Clinical Nutrition 41; Jun. 1985; pp. 1201–1209; "Relationship between zinc and prostaglandin metabolisms in plasma and small intestine or rats".

M.K. Song, et al.; Life Sciences, vol. 42, pp. 687–694; "Intestinal Zinc Transport: Influence of Streptozotocin–Induced Diabetes, Insulin and Arachidonic Acid".

R. Paul Robertson, M.D.; Symposium on Prostaglandins; Medical Clinic of North American, vol. 65, No. 4, Jul. 1981; "Prostaglandins, Glucose Homeostasis, and Diabetes Mellitus".

M.K. Song, et al.; Prostaglandins Leukotrienes and Medicine 17: 159–166, 1985; "Effect of Oral Administration of Arachidonic Acid on Prostaglandin and Zinc Metabolism in Plasma and Small Intestine of the Rat".

Buxade Vinas, Chem. Abstracts CA107(5):39206z, 1985.

Buxade Vinas, Chem. Abstracts CA107(5):39205y, 1985.

Rosetti et al., Chem. Abstracts CA114(9):75015q, 1990.

Micossi et al., Chem. Abstracts CA91(11):83900w, 1978.

T. Pham et al., "Factors Affecting Zinc Flux Rates of Rat Intestinal Segments Mounted in Ussing Chambers," Biochem. Arch. 7:213–219 (1991).

M. K. Song & A. D. Mooradian, "Intestinal Zinc Transport: Influence of Streptozotocin–Induced Diabetes, Insulin and Arachidonic Acid," *Life Sci.* 42:687–694 (1988).

C. K. Lardinois & G. H. Starich, "Polyunsaturated Fats Enhance Peripheral Glucose Utilization in Rats," *J. Am. Coll. Nutr.* 10:340–345 (1991).

M. K. Song & N. F. Adham, "Evidence for an Important Role of Prostglandins $E_2$ and $F_2$ in the Regulation of Zinc Transport in the Rat," *J. Nutr.* 109:2152–2159 (1979).

M. K. Song & N. F. Adham, "Metabolic Influences on Intestinal Zinc Uptake in Rats," *Biochem. Arch.* 1:75–83 (1985).

S. Southon et al., "Hexose Transport and Mucosal Morphology in the Small Intestine of the Zinc–Deficient Rat," *Br. J. Nutr.* 52:371–380 (1984).

M. K. Song & N. F. Adham, "Relationship Between Zinc and Prostaglandin Metabolisms in Plasma and Small Intestine of Rats," *Am. J. Clin. Nutr.* 41:1201–1209 (1985).

M. Song & N. F. Adham, "Role of Prostaglandin $E_2$ in Zinc Absorption in the Rat," *Am. J. Physiol.* 234:E99–105 (1978).

G. Y. Luh and M. K. Song, "Characterization of the Low Mol. Wt. Zinc–Binding Ligand from Rat Small Intestine by Comparison to the Organic Zinc–Binding Ligands," *Comp. Biochem. Physiol.* 91B:569–576 (1988).

M. K. Song et al., "Evidence for a Role of Prostaglandins in the Regulation of Intestinal Zinc Transport," *Nutr. Rep. Int'l.* 32:71–83 (1985).

D. W. Watkins et al., "Zinc Inhibition of Glucose Uptake in Brush Border Membrane Vesicles from Pig Small Intestine," *Pflügers Arch.* 415:165–171 (1989).

M. K. Song et al., "Influence of Prostaglandins on Unidirectional Zinc Fluxes Across the Small Intestine of the Rat," *Br. J. Nutr.* 59:417–428 (1988).

"The Astonishing Benefits of Chromium Picolinate" (brochure).

PROSTATE EXTRACT SUPPLEMENTED WITH ZINC

RELATED APPLICATION

This application is a 371 of PCT/US94/02909 and is a continuation-in-part of U.S. application Ser. No. 08/179,761, filed Jan. 7, 1994, now issued as U.S. Pat. No. 5,411,748, which is a continuation of application Ser. No. 07/964,879, filed Oct. 22, 1992, now abandoned.

UNITED STATES GOVERNMENT INTEREST IN THE INVENTION

This invention was made with United States Government support; namely, the facilities, equipment, and materials of the Department of Veterans Affairs. The U.S. Government has certain rights in this invention in the United States.

FIELD OF THE INVENTION

The present invention relates to compositions and pharmaceutical preparations that contain zinc prostate extract supplemented with zinc

BACKGROUND OF THE INVENTION

Diabetes is one of the most common metabolic disorders in humans. Indeed, nearly 1 million Americans are afflicted with juvenile-onset diabetes. This form of the disease is also known as insulin-dependent or Type I diabetes, and usually appears abruptly during childhood or young adulthood. Type II, or non-insulin-dependent diabetes is characterized by a less abrupt onset. Type II diabetes commonly occurs beyond the age of 40 or so. Both types of diabetes impair the body's ability to access blood glucose for use as an energy source. Chronically high levels of blood sugar gradually damage many tissues and organs of the body.

Substantial efforts have been directed toward understanding the causes and consequences of diabetes. A strong autoimmune component is now believed important in the etiology of type I diabetes (see *Science* 225:1381 (1984), and Immunology Today 5:230 (1984)). The metabolic consequences of experimentally induced diabetes have also been explored. For example, in *Diabetes* 31:426 (1982) Schneir et al. demonstrated that collagen, an important structural protein of skin, has a significantly decreased half-life in diabetic rats. It is well appreciated that both forms of diabetes impact the tissues of the body in a global fashion.

Despite the availability of insulin treatment, diabetes remains a serious disease that is responsible for many deaths and substantial morbidity worldwide. For example, the life-span of the average diabetic is shortened by as much as 50%. Although insulin treatment can assist in regulating blood sugar levels, the degree of this control is typically insufficient to prevent many of the sequelae from diabetes. The consequences from long term diabetes can include eye damage, often leading to blindness; circulatory problems; problems with wound healing; and other serious consequences. Improved treatments for diabetes are urgently required.

SUMMARY OF THE INVENTION

One aspect of the present invention is a composition of matter comprising a crystalline zinc chelated with extract of animal prostate tissue.

Another aspect of the present invention is a pharmaceutical composition that can be administered to a mammal. This pharmaceutical composition comprises crystalline zinc chelated with extract of animal prostate tissue and at least one pharmaceutically acceptable excipient. The composition can take the form of either a tablet or capsule. Each tablet or capsule of this composition preferably contains from about 20 to 150 milligrams of zinc.

A further aspect of the present invention is a method of treating diabetes. According to this method, a pharmaceutical composition that comprises a zinc chelated prostate extract is administered to a diabetic mammal in a quantity sufficient to reduce blood glucose concentration in that mammal.

Yet a further aspect of the present invention regards a pharmaceutical composition comprising an extract of animal prostate tissue for use in the treatment of diabetes. In a preferred embodiment, the pharmaceutical composition also comprises zinc.

Another aspect of the present invention is the use of an organic extract of animal prostate tissue in the preparation of a medicament for the treatment of diabetes.

Another aspect of the present invention is the use of prostate extract for the treatment of diabetes. The extract is preferably supplemented with zinc. Prostate extract can also be used in the preparation of a medicament for the treatment of diabetes. In one embodiment, the prostate tissue comprises a first group of molecules that are soluble in petroleum either or hexane. A subset of the molecules that are soluble in petroleum either or hexane is present in the prostate tissue. The prostate tissue also comprises a second group of molecules that are soluble in ethyl acetate or chloroform. The extract of animal prostate tissue can be obtained by a process comprising first mincing the tissue, and resuspending the minced tissue in an aqueous solution. A first group of molecules can then be extracted from the resuspended tissue using a first, nonpolar solvent that is less polar than petroleum either and hexane. The first solvent containing the first group of molecules can then be discarded. The second group of molecules can then be extracted using a second solvent that is more polar than the first solvent. Finally, the desired prostate extract can be created by removing the second solvent.

DETAILED DESCRIPTION OF THE INVENTION

Introduction

Figure 1:
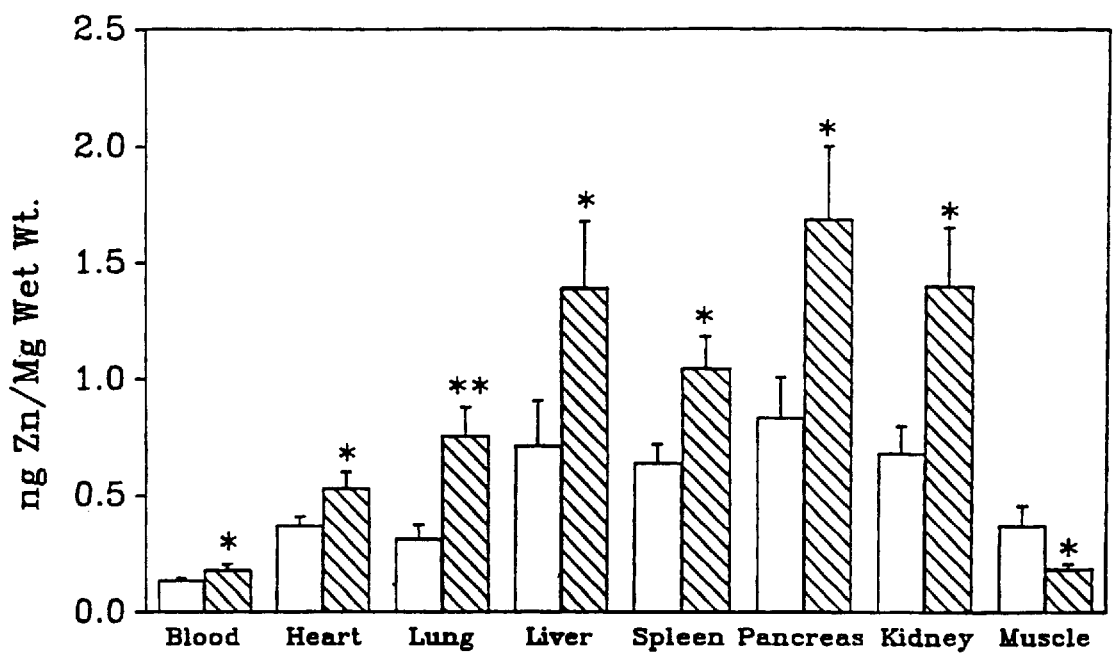
FIG. 1 shows the zinc concentrations of organ tissues of normal rats with and without prostate extract treatment. The open bars indicate without prostate extract and the cross-hatched bars indicates with prostate extract. In this figure, * indicates P<0.05 and ** indicates P<0.001.

I have discovered that a composition of matter comprising a zinc chelated with extract of animal prostate tissue is useful for the treatment of diabetes. This composition may also be useful in treating other conditions that affect zinc and essential fatty acid metabolism.

For at least 60 years, the biomedical community has appreciated the fact that zinc metabolism is altered as a consequence of the diabetic condition. For example, in *J. Clin. Invest.* 17:725 (1938), Scott et al. showed that zinc is essential for insulin storage in the pancreatic B-cells of humans. In *Virchows Arch.* B4:94–302 (1970), Engelbart and Kief showed that acute stimulation of insulin secretion in rats reduced the zinc content in the B-cells of their pancreata. It is also well known that zinc participates in the storage of insulin, and that the amount of insulin stored during zinc deficiency is less than when zinc levels are normal. Thus, the important relationship between zinc metabolism and diabetes has been clearly established in the scientific literature.

An experimental finding presented under Example 1 confirmed that enhanced survival of diabetic test animals correlated with increased levels of dietary zinc. Based on this observation, I hypothesized that a dietary supplement which facilitated zinc utilization would also provide benefits to diabetic patients.

I considered prostaglandin precursors as possible diabetes therapeutic agents that could improve the symptoms associated with diabetes. My investigations concentrated on these substances because Song and Adham had previously demonstrated that at least some prostaglandins ($PGE_2$) can act as zinc-binding ligands (*J. Nutrition* 109:2152 (1979)). The authors of this report also showed that other prostaglandins ($PGA_2$ and $PGB_2$) had no influence on zinc transport. Thus, only a subset of prostaglandins effectively chelated zinc, or otherwise influenced zinc transport. Additionally, in *Life Sciences* 42:687 (1988), Song and Mooradian speculated that arachidonic acid, a prostaglandin precursor, played a role in the control of zinc flux across the intestinal epithelium of diabetic rats. Arachidonic acid is another example of a prostaglandin precursor.

Although it would seem desirable to alleviate diabetic symptoms by directly administering an appropriate prostaglandin, this approach is impractical. The fact that prostaglandins have very short half-lives prohibits their use as therapeutics.

Since prostaglandins are synthesized from unsaturated fatty acid precursors, I focused on these latter compounds as candidates for diabetes therapeutics. Furthermore, my search concentrated on sources of unsaturated fatty acids that could be administered as dietary supplements. Altogether, three different sources of unsaturated fatty acids were tested as diabetes therapies.

The results from side-by-side comparisons of arachidonic acid, evening primrose oil, and a novel extract of animal prostate tissue indicated marked differences between the effectiveness of these agents as diabetes therapeutics. Specifically, the extract of animal prostate tissue most effectively lowered blood glucose, and raised cytosolic tissue glucose concentrations in experimental rats.

Most significantly, my investigations demonstrated that encapsulated zinc chelated prostate extract lowered the blood glucose readings of diabetic humans. This finding confirmed the effectiveness of this novel composition as a viable diabetes therapy.

I. Crystalline Zinc Chelated with Prostate Extract

One aspect of the present invention is zinc chelated with prostate extract; i.e., crystals in which negatively charged fatty acids that are present in an organic extract of prostate tissue are bound by positively charged zinc ions.

Preferably, the organic extract of prostatic tissue contains unsaturated fatty acids that comprise essential fatty acids. The essential fatty acids preferably are selected from the group consisting of prostaglandins and prostaglandin precursors. These fatty acids can be obtained from the prostates of animals such as the cow, sheep, or goat. The extraction can be accomplished by resuspending the prostates in a buffered aqueous solution, extracting the saturated fatty acids with a highly nonpolar organic solvent such as petroleum ether or hexane, extracting unsaturated fatty acids with a more polar organic solvent such as ethyl acetate or chloroform, and then adding a zinc salt in a quantity sufficient to chelate the fatty acids or amino acids present.

II. Pharmaceutical Compositions

Further aspects of the present invention regard pharmaceutical compositions. Pharmaceutical compositions, according to the present invention, contain: (1) an extract of animal prostate tissue, (2) a zinc salt such as zinc sulfate, (3) a protein hydrolysate, and (4) at least one pharmaceutically acceptable excipient.

The protein hydrolysate may be in the form of amino acids or incompletely hydrolyzed proteins such as proteoses, peptones, or other partially hydrolyzed proteins, such as albumin.

The pharmaceutical compositions prepared according to the present invention preferably contain essential fatty acids, zinc sulfate, and protein hydrolysate in a ratio of about 10:1:5 by weight. The pharmaceutical compositions can be packaged in tablet or capsule form by procedures that are well known in the pharmaceutical arts. Preferably, each tablet or capsule contains about 200 mg of prostate extract, about 20 mg of zinc and about 100 mg of protein hydrolysate, in addition to the pharmaceutically acceptable excipient or excipients. Suitable excipients for tablets and capsules include inert diluents, such as calcium carbonate, sodium carbonate or bicarbonate, lactose, or calcium phosphate; or binding agents, such as starch, gelatin, or acacia; or lubricating agents, such as magnesium stearate, stearic acid, or talc. The coating of the capsules can be gelatin or a soluble polymer, as is well understood in the art. The tablets or capsules are suitable for oral administration.

The pharmaceutical compositions described herein are useful for the treatment of diabetes, hypertension, impotence, and other diseases in which zinc or prostaglandin metabolism is impaired. In particular, diabetes can be treated by administering the zinc chelated prostate extract of the present invention to a diabetic mammal in a quantity sufficient to reduce blood glucose concentration in the mammal. Typical doses for patients with diabetes or hypertension, stated as the quantity of zinc, are from about 80 mg to about 150 mg of zinc. These doses can be adjusted by one of ordinary skill in the art according to such factors as the weight, age, sex, and state of health of the patient, as well as according to the response to a particular dosage.

Figure 2:
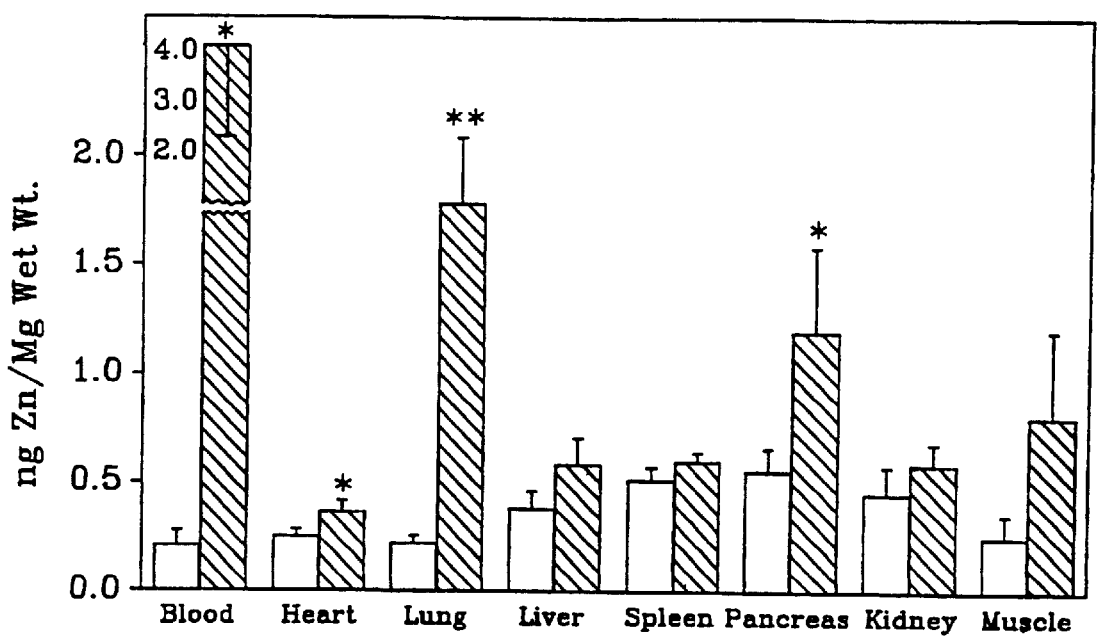
FIG. 2 shows zinc concentrations of organ tissues of diabetic rats with and without prostate extract treatment. The open bars indicate without prostate extract and the cross-hatched bars indicates with prostate extract. In this figure, * indicates P<0.05 and ** indicates P<0.001.

In the experiments illustrated in FIGS. 1 and 2, rats were anesthetized and then given 200 mg of prostate extract plus 200 μg zinc in 2 ml distilled water by intragastric intubation two hours before sacrifice. All the values are means ±SEM of six determinations. It can be seen that the prostate extract composition had a dramatic effect on zinc concentrations in all tissues tested in normal rats and on blood, heart, lung and pancreas of diabetic rats.

Figure 3:
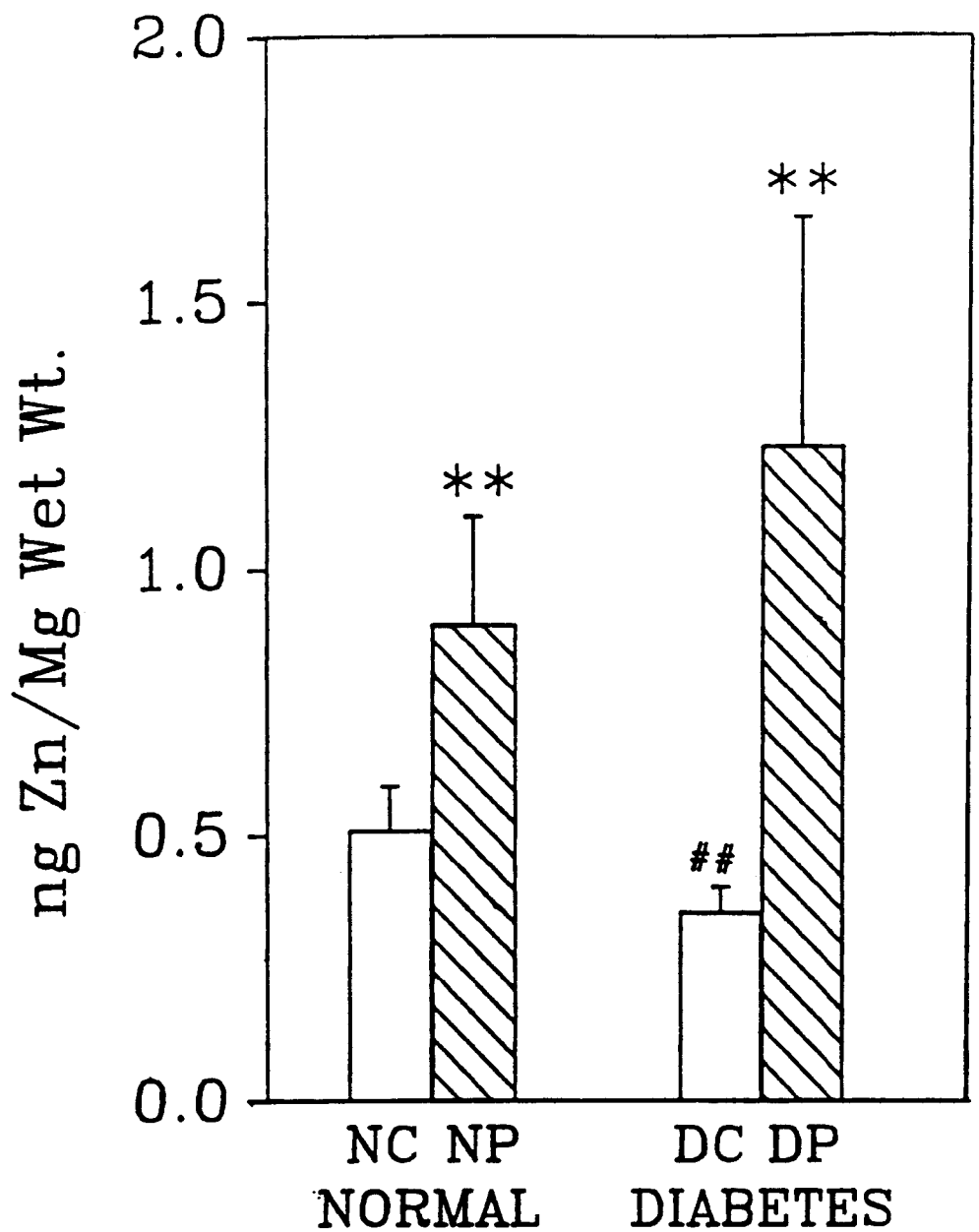
FIG. 3 shows a comparison of zinc concentrations in organ tissues of normal and diabetic rats with and without prostate extract. NC refers to normal rats without prostate extract treatment. NP refers to normal rats with prostate extract treatment. DC refers to diabetic rats without protate extract treatment. DP refers to diabetic rats with prostate extract treatment. In this figure, ** indicates P<0.001 when the values of protate extract treated rats are compared with those of untreated rates, and ## indicates P<0.001 when the values of diabetic rats are compared with those of normal rats.

FIG. 3 shows a comparison of zinc concentrations in organ tissues of normal and diabetic rats with and without prostate extract from the data shown in FIGS. 1 and 2. The mean values of tissue zinc concentrations in normal and diabetic rats treated with and without prostate extract were compared. It can be seen that there is a significant difference between normal and diabetic rats and also that prostate extract had a significant effect on both normal and diabetic rats.

The experiment described below in Example 1 illustrates a fundamental relationship between the level of dietary zinc consumption and longevity in diabetic rats. In this procedure, laboratory rats were made diabetic by injection with a chemical agent that is well known in the art. The diabetic rats were then fed diets that provided zinc in amounts that ranged from inadequate to excessive. The results from this simple experiment confirmed that dietary zinc influenced the life span of diabetic test animals.

EXAMPLE 1

Effect of Dietary Zinc on the Survival of Diabetic Rats

Fifty-one rats were divided into three groups of 17 rats each. All of the rats were made diabetic by injection of streptozotocin (50 mg/kg). One week later the three groups of rats were fed diets having defined quantities of zinc. The first group was fed a zinc-deficient diet (1 $\mu$g Zn/g), the second group was fed a zinc-adequate diet (37.5 $\mu$g Zn/g), and the third group was fed a diet containing excess zinc (1 mg Zn/g). The number of surviving rats was counted after 25 days. The results presented in Table 1 summarize the survival of the test animals in this experiment.

TABLE 1

THE SURVIVAL RATE OF DIABETIC RATS FED WITH DIFFERENT CONCENTRATIONS OF ZINC
SURVIVAL RATES (No of Survived rats/No of diabetic rats)

| (1 $\mu$g Zn/g) Zinc-Deficient | (37.5 $\mu$g Zn/g) Zinc-Adequate | (1 mg Zn/g) Zinc-Excess |
| --- | --- | --- |
| 8/17 | 11/17 | 15/17 |

Example 2 describes the procedure that was used to isolate unsaturated fatty acids from animal prostate tissue. Prostate tissue contains zinc, prostaglandins, essential fatty acids, citric acid, testosterone and proteins. However, there is no evidence to indicate that an organic extract of prostate tissue is limited to these substances.

EXAMPLE 2

Preparation of Crystalline Zinc Chelated Prostate Extract

Bovine prostates were obtained from a slaughterhouse, minced into small pieces and frozen at −70° C. The sliced tissue was suspended in a 10-fold excess (w/v) of 6.0 mM Tris-HCl buffer, pH 8.0, disrupted with a VIRTIS-45 homogenizer (Virtis Co., Gardner, N.Y.), and centrifuged at 4° C. for 20 minutes at 3,000×g. The upper part of the fat was removed physically, and the supernatant was incubated at 37° C. for one hour. The saturated fatty acids were extracted with petroleum ether. The remaining aqueous solution, which included unsaturated fatty acids, was acidified to pH 3.0 with 0.2 N HCl, and the unsaturated fatty acid mixture including prostaglandins was extracted 2 to 3 times with one volume each time of ethyl acetate mixed with isopropanol (1:1 v/v) or chloroform. The ethyl acetate or chloroform extracts were then combined. The unsaturated fatty acid solutions were either freeze-dried or evaporated to dryness under vacuum. The oil-like prostate extract that resulted from these procedures included unsaturated fatty acids. A preparation of zinc chelated unsaturated fatty acids was formed by mixing 200 mg of prostate extract with 20 mg zinc chloride and 100 mg of protein hydrolysate that was purchased from Sigma (St. Louis, Mo.).

Example 3 describes a procedure that was used to assess the effects of arachidonic acid, evening primrose oil and prostate extract on the symptoms of diabetic rats. Three sources of unsaturated fatty acids were tested for their relative abilities to improve the symptoms of diabetic rats. Arachidonic acid and evening primrose oil were two of the substances used in making this comparison. Evening primrose oil is known to be a rich source of both linoleic acid and linolenic acid. I also prepared and tested an organic extract of animal tissue as a source of unsaturated fatty acids that could positively influence diabetic symptoms in rats. All of the substances were administered as dietary supplements in conjunction with a dissolved zinc salt. My findings indicated the prostate extract most advantageously influenced the symptoms of diabetic rats.

EXAMPLE 3

Investigation of the Effects of Unsaturated Fatty Acids on the Symptoms of Diabetic Rats Rats were first made diabetic by injection with streptozotocin. These diabetic rats Were then administered one of three unsaturated fatty acid preparations in their drinking water. The drinking water contained dissolved zinc sulfate together with either arachidonic acid, evening primrose oil or prostate extract that was prepared in accordance with the method of Example 2. The zinc sulfate solution was diluted to provide a final concentration of 10 mg/l of zinc. The arachidonic acid and prostate extract were each diluted to final concentrations of 100 mg/l. The evening primrose oil was diluted to a final concentration of 500 mg/l. The zinc and prostate extract concentrations used in this procedure were chosen to proportionally approximate a dosage that would be given to an adult human. In calculating the concentrations, I assumed that a 60 kg diabetic human would consume a daily dosage of 600–1000 mg of prostate extract and 60–100 mg zinc. This amounted to 10 mg of prostate extract and 1 mg of zinc per kg of body mass. The estimated daily water consumption for a normal rat was 40 ml. At 18 days post-streptozotocin injection, blood glucose measurements were recorded for all test animals using a GLUCOMETER ELITE (Miles Co.). The results of these glucose measurements are presented in Table 2.

TABLE 2

BLOOD GLUCOSE CONCENTRATION (in mg/100 ml) IN
DIABETIC RATS CHANGES AFTER CONSUMING WATER
CONTAINING DIFFERENT CONSTITUENTS

| Experimental Conditions | Initial Values | Final Values | Improved Values |
|---|---|---|---|
| Normal Rats | 83.6 ± 2.6 | | |
| D-18d-Zn-PE | 495.0 ± 24.7 | 341.4 ± 17.4 | 153.6 ± 10.5 |
| D-18d-Zn-AA | 435.6 ± 24.7 | 353.4 ± 10.9 | 91.6 ± 24.4* |
| D-18d-Zn-EPO | 355 | 418 | −63 |
| D-18d-Zn only | 374.2 ± 37.6 | 377.0 ± 43.3 | 0.8 ± 24.3** |
| D-18d-DW | 321 | 359 | −48 |

*$P < 0.05$ compared to the values of D-18d-Zn-PE
**$P < 0.05$ compared to the values of D-18d-Zn-PE
D-18d = 18 days after induction of diabetes
Zn-PE = Drinking water contained 10 mg Zn plus 100 mg of prostate extract/liter
Zn-AA = Drinking water contained 10 mg Zn plus 100 mg of arachidonic acid/liter
D-18d-EPO = Drinking water contained 8 mg Zn plus 500 mg of Evening Primrose oil/liter
Zn-only = Drinking water contained 10 mg Zn/liter
DW = Distilled water The results shown in Table 2 confirmed that diabetic animals had significantly higher blood glucose levels than normal rats. Administration of zinc alone to diabetic rats did not effect blood glucose levels. Dietary administration of zinc together with evening primrose oil was also ineffective in reducing the blood glucose concentration of the diabetic animals. The combination treatment of zinc and arachidonic acid moderately reduced blood glucose concentrations. Surprisingly, the reduction of blood glucose that followed administration of zinc and prostate extract was clearly more pronounced than for any other treatment.

That prostate extract should efficiently reduce the blood glucose concentration of diabetic animals while evening primrose oil and arachidonic acid were ineffective or moderately effective, was an unexpected result. Significantly, this finding demonstrated that all sources of unsaturated fatty acids are not equal in their capacities to improve diabetic symptoms.

To independently assess a second indicator of the diabetic condition, cytosolic glucose concentrations were determined for various tissues in diabetic rats that had undergone various dietary supplementations. Example 4 presents the results of such determinations that were made using rats treated exactly as described under Example 3.

EXAMPLE 4

Cytosolic Glucose Concentrations in Various Tissues of Diabetic Rats

Immediately following sacrifice of the experimental animals from Example 3 by injection of nembutal (50 mg/kg), various tissues were isolated and stored at −70° C. Each tissue was disrupted in a polytron homogenizer and then centrifuged at 2,000×g for 20 minutes. The supernatants were either stored frozen or immediately used for determining glucose and protein concentrations. Glucose concentrations were measured using a model A23 glucose analyzer that was purchased from Yellow Springs Instruments Co. (Yellow Springs, Ohio). Protein concentrations were determined according to the method described by Lowry et al. in *J. Biol. Chem.* 193:265 (1951). The values obtained for the glucose readings were divided by the protein concentration readings to normalize the measurements. This normalization was necessary to control for the variable masses and protein yields that distinguished batches of different tissues. The results are shown in Table 3.

TABLE 3

GLUCOSE CONCENTRATIONS OF DIFFERENT ORGAN CELL
CYTOSOLS OF DIABETIC RATS FED DIFFERENT DIETS

| | Glucose Concentration (mg glucose/mg protein) | | | | |
|---|---|---|---|---|---|
| Organs | Zinc plus PE | Zinc plus AA | Zinc Only | Zinc plus EPO | Dist. Water |
| Heart | 184.3 ± 19.6 | 151.8 ± 14.0 | 111.9 ± 15.8* | 86.4 | 97.0 |
| Lung | 64.3 ± 9.5 | 59.3 ± 6.3 | 57.9 ± 10.3 | 56.8 | 51.0 |
| Liver | 181.8 ± 26.4 | 149.7 ± 22.O* | 122.1 ± 17.5* | 123.1 | 124.4 |
| Pancreas | 152.8 ± 11.1 | 126.0 ± 6.4# | 128.4 ± 12.2# | 89.6 | 112.2 |
| Spleen | 131.0 ± 3.6 | 103.1 ± 7.4** | 123.2 ± 9.1 | 123.1 | 124.4 |
| Kidney | 200.8 ± 15.4 | 157.5 ± 12.7# | 150.8 ± 11.5* | 119.3 | 118.9 |
| Muscle | 638.5 ± 67.0 | 398.5 ± 41.2** | 383.0 ± 43.7** | 317.7 | 338.5 |
| Intest. | 970.2 ± 74.0 | 685.6 ± 90.1* | *792.8 ± 94.3# | 605.4 | 702.2 |
| Total Ave. | 315.5 ± 112.2 | 228.9 ± 74.4* | 233.8 ± 86.9* | 190.2 ± 65.6 | 208.6 ± 76.7 |

Significant at $P = 0.05$ when compared the values of those rats given water containing prostate extract (PE) plus zinc.
*Significant at $P < 0.05$ when compared the values of those rats given water containing PE plus zinc.
**Significant at $P < 0.01$ when compared the values of those rats given water containing PE plus zinc.

The results in Table 3 indicated a correlation between dietary supplementation with prostate extract and enhanced glucose uptake at the cellular level. Whereas diabetic tissues typically had low levels of free glucose, my results showed this level was dramatically increased in test animals that received the combination of prostate extract and zinc. Dietary administration of either arachidonic acid or evening primrose oil in combination with zinc had no effect on cytosolic glucose concentrations. The next step in the development of my invention was to extend the use of zinc chelated prostate extract beyond the treatment of laboratory animals.

The effectiveness of prostate extract in alleviating the symptoms of diabetic humans was also investigated. Example 5 describes changes in blood glucose concentrations that were recorded for diabetic volunteers after dietary supplementation with capsules that contained zinc chelated prostate extract.

EXAMPLE 5

Effect of Dietary Administration of Prostate Extract on Blood Glucose levels of Diabetic Humans Sixteen diabetic individuals were identified and recruited as volunteers to test the effects of dietary supplementation with zinc chelated prostate extract. Initial blood glucose readings were taken for all individuals using a GLUCOMETER ELITE (Miles Co.). All 16 volunteers then consumed encapsulated zinc chelated prostate extract 2–4 times each day for a period of 1 to 3 months. Each capsule contained 200 mg of prostate extract, 20 mg of zinc and gelatin. These capsules were prepared by Banner Pharmacap Co. (Chatsworth, Calif.) using zinc chelated prostate extract prepared according to the method detailed under Example 2. At the end of the test period, blood glucose measurements were repeated for all subjects. Table 4 summarizes the results of all blood glucose readings in this experiment.

TABLE 4

BLOOD GLUCOSE CONCENTRATIONS OF MILD DIABETIC PATIENTS AFTER THE INTAKE OF BOVINE PROSTATE EXTRACT SUPPLEMENTED WITH ZINC CAPSULE

| Patient Initials | Patient Age | Patient Sex | Range of Glucose Concentration Before Zinc Intake | Range of Glucose Concentration After Zinc Intake |
|---|---|---|---|---|
| JSS | 56 | F | 190–190 mg/100 ml | 90–135 mg/100 ml |
| KIM | 76 | F | 270–370 mg/100 ml | 95–179 mg/100 ml |
| SHK | 63 | M | 180–280 mg/100 ml | 120–180 mg/100 ml |
| DHS | 61 | F | 180–280 mg/100 ml | 130–170 mg/100 ml |
| HGL | 59 | M | 150–240 mg/100 ml | 100–160 mg/100 ml |
| HKK | 57 | M | 180–280 mg/l00 ml | 130–180 mg/100 ml |
| SBS | 61 | M | 200–290 mg/100 ml | 130–200 mg/100 ml |
| SES | 62 | M | 180–250 mg/100 ml | 130–210 mg/100 ml |
| CLC | 64 | M | 150–260 mg/100 ml | 90–160 mg/100 ml |
| JJK | 49 | F | 280–320 mg/100 ml | 180–240 mg/100 ml |
| BSK | 59 | M | 210–350 mg/100 ml | 150–210 mg/100 ml |
| JAK | 51 | M | 160–250 mg/100 ml | 100–190 mg/100 ml |
| KUK | 59 | M | 180–260 mg/100 ml | 140–210 mg/l00 ml |
| ESL | 58 | F | 150–240 mg/100 ml | 110–180 mg/100 ml |
| PHL | 62 | M | 180–250 mg/100 ml | 110–160 mg/l00 ml |
| HSC | 78 | F | 210–310 mg/100 ml | 150–210 mg/100 ml |
| The Means ± SEM of mid points of each value: | | | 236.56 ± 9.19 | 152.43 ± 6.88 |

Paired t statistics of the two med-points of each value is $P < 0.0001$.

Glucose clearance rates were also measured for diabetic patients before and after a regimen of dietary administration with zinc chelated prostate extract. In this experiment, I measured the rate at which a defined amount of glucose is removed from the blood stream of diabetic individuals. Whereas non-diabetics typically exhibit rapid glucose clearance rates, diabetic individuals exhibit lower rates. These lower rates of glucose clearance result from the diminished insulin activity that characterizes the diabetic condition. An increased rate of glucose clearance that followed administration of zinc chelated prostate extract indicates a therapeutic effect.

The advantage of using blood glucose clearance rate as an indicator of efficacy is that this test is not influenced by temporal changes of diet or exercise whereas blood glucose levels are effected. For this reason, comparison of blood glucose clearance rates before and after a regimen of dietary administration of zinc chelated prostate extract is believed to most accurately measure the positive effects of the therapeutic regimen.

Example 6 details the procedure used to measure the effect of dietary administration of zinc chelated prostate extract on the glucose clearance rates of diabetic volunteers.

EXAMPLE 6

The Effect of Zinc Chelated Prostate Extract on the Glucose Clearance Rates of Diabetic Patients Four diabetic volunteers were first identified at the Sepulveda V.A. Medical Center. After stabilizing their carbohydrate intakes at a level of 150–200 grams/day for a period of 3 days, glucose clearance rates were determined after drinking a 225 ml volume of solution that contained 75 grams of glucose. Blood glucose measurements were then taken at 0, 30, 60, 90, 120, 150 and 180 minutes after consuming the glucose solution. Blood glucose measurements were made using a ONE-TOUCH II GLUCOMETER (Lifescan, Inc., Milpitas, Calif.). The clearance rate was determined as the rate at which the glucose concentration decreased after having reached a maximal concentration.

After establishing the initial blood glucose clearance rates, three randomly selected volunteers consumed 4 capsules of zinc chelated prostate extract each day for a period of 3 months. The composition of the capsules used in this procedure was exactly as described under Example 5. The fourth diabetic volunteer was given a placebo. At the end of the 3 month trial period, blood glucose clearance rates were again determined for all volunteers. The quantitative results of this procedure are presented in Table 5.

TABLE 5

GLUCOSE TOLERANCE TEST (mg Glucose/100 ml blood samples)

| Patients # | Gel Capsules | Initial GCR | Final GCR | Difference | % of Change |
|---|---|---|---|---|---|
| 1. | Test Capsules | 11 | 32 | 21 | 190.9 |
| 2. | Test Capsules | 57 | 75 | 18 | 31.6 |
| 3. | Test Capsules | 48 | 59 | 11 | 22.9 |
| 4. | Placebo | 102 | 95 | −7 | −6.8 |
| 5. | Placebo | 21 | 20 | −1 | −4.8 |

The results presented in Table 5 indicated the glucose clearance rates of all diabetic volunteers were substantially improved after a 3 month period of consuming zinc chelated prostate extract. A patient who received a placebo treatment showed no such improvement. Because the patient that received the placebo was only mildly diabetic, his initial glucose clearance rate was more nearly normal than any of the other volunteers.

Interestingly, the patient receiving the placebo in this test exhibited a decreased glucose clearance rate over the period of the experiment. This represents an ordinary trend for such a patient, since the glucose clearance rate becomes progressively lower as the disease becomes progressively more severe.

The findings presented here indicated that dietary supplementation with zinc chelated prostate extract improved the symptoms associated with diabetes. Although the mechanism by which prostate extract leads to improved symptoms in diabetic animals and man is not clearly understood, the powerful effects of prostate extract on the increased intestinal zinc absorption may be contributory. Regardless of the mechanism, I have demonstrated that dietary supplementation with prostate extract produces superior results with regard to improving diabetic symptoms when compared to regimens that include dietary administration with zinc, either alone or in combination with other examples of unsaturated fatty acids.

The present invention provides compositions that are convenient sources of both zinc and essential fatty acids. This composition can be used as a dietary supplement or treatment for diabetes or other conditions. Because the metabolism of zinc and the metabolism of essential fatty acids, including prostaglandin precursors, are interlinked, the use of such compositions is more effective than is the use of either zinc or fatty acids alone in treating diabetes.

I claim:

1. A pharmaceutical composition, comprising:
   (a) a zinc chelated extract of animal prostatic tissue; and
   (b) at least one pharmaceutically acceptable excipient, said pharmaceutical composition having the form of a tablet or a capsule.

2. The pharmaceutical composition of claim 1 wherein each tablet or capsule contains about 20 milligrams of zinc.

3. The pharmaceutical composition of claim 1 wherein each tablet or capsule contains from about 20 milligrams of zinc to about 150 milligrams of zinc.

4. A method of treating diabetes comprising administering the composition of claim 1, to a diabetic mammal in a quantity sufficient to reduce blood glucose concentration in a mammal.

5. A composition for use in the treatment of diabetes comprising an extract of animal prostate tissue and zinc in the form of a tablet or capsule.

6. A method for treatment of diabetes of a mammal, comprising administering to the mammal an amount an extract of animal prostate tissue effective for treatment of diabetes.

7. The method of claim 6, wherein said extract of animal prostate tissue is zinc-chelated.

8. The composition of claim 5, wherein said composition is crystalline zinc chelated extract of animal prostate tissue.

* * * * *

UNITED STATES PATENT AND TRADEMARK OFFICE
CERTIFICATE OF CORRECTION

PATENT NO. : 5,997,908
DATED : November 2, 1999
INVENTOR(S) : Mark Edward Nichols It is certified that error appears in the above-identified patent and that said Letters Patent is hereby corrected as shown below:

Column 3,
Line 55, insert -- . -- after "performed"

Column 8,
Line 31, insert -- , -- after "1"

Signed and Sealed this

Twenty-fourth Day of September, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 5,997,908
DATED : December 7, 1999
INVENTOR(S) : Moon K. Song

It is certified that error appears in the above-identified patent and that said Letters Patent is hereby corrected as shown below:

This certificate supersedes Certificate of Correction issued September 24, 2002, the number was erroneously mentioned and should be deleted since no Certificate of Correction was granted.

Signed and Sealed this

Fifth Day of November, 2002

*Attest:*

*Attesting Officer*

JAMES E. ROGAN
*Director of the United States Patent and Trademark Office*